United States Patent [19]
Ohnishi

[11] Patent Number: 4,975,971
[45] Date of Patent: Dec. 4, 1990

[54] METHOD AND APPARATUS FOR DETECTING SIGNIFICANT DIFFERENCE OF SHEET MATERIAL

[75] Inventor: Ryuji Ohnishi, Takamatsu, Japan

[73] Assignee: Futec Inc., Takamatsu, Japan

[21] Appl. No.: 208,097

[22] Filed: Jun. 17, 1988

[30] Foreign Application Priority Data

Oct. 14, 1987 [JP] Japan ................. 62-258683

[51] Int. Cl.⁵ .............................. G06K 9/00
[52] U.S. Cl. ...................... 382/8; 356/237; 358/106; 382/34; 382/47
[58] Field of Search ............ 382/8, 34, 1, 47; 358/106; 356/237

[56] References Cited

U.S. PATENT DOCUMENTS

| | | | |
|---|---|---|---|
| 4,614,430 | 9/1986 | Hara et al. | 382/8 |
| 4,724,481 | 2/1988 | Nishioka | 358/106 |
| 4,776,466 | 10/1988 | Yoshida | 358/106 |

Primary Examiner—Leo H. Boudreau
Attorney, Agent, or Firm—Joseph Scafetta, Jr.

[57] ABSTRACT

A method of detecting a significant difference of a to-be-checked sheet includes the steps of: scanning a traveling to-be-checked sheet by a camera in the widthwise direction to obtain image data, extracting an outline of an image and an outline of a defect on the to-be-checked sheet from the image data, sequentially writing the outline data extracted in the outline extraction step in a memory with a predetermined cycle in accordance with travel position data and simultaneously reading out the outline data, comparing outline pattern data for an immediately preceding cycle as outline mask data with the latest outline pattern data obtained in a cycle following the immediately preceding cycle, and detecting a significant difference between the outline mask data and the latest outline pattern data in accordance with the comparison result obtained in the comparison step.

14 Claims, 3 Drawing Sheets

METHOD AND APPARATUS FOR DETECTING SIGNIFICANT DIFFERENCE OF SHEET MATERIAL

CROSS-REFERENCE TO RELATED APPLICATION

This application is related to U.S. Patent Application Ser. No. (07/207,969) filed concurrently herewith on June 17, 1988, in the name of the same inventor for an invention entitled "Method and Apparatus for Detecting Disparity of Cyclic Length of Printed Patterns".

BACKGROUND OF THE INVENTION

1. Field of the Invention

The present invention relates to a method and apparatus for detecting a defect on a surface of a to-be-checked sheet on which images such as letters, patterns, and the like are cyclically printed in the longitudinal direction.

2. Description of the Related Art

For example, images such as letters (e.g., a hospital's name) and patterns are printed on a sheet for packing a drug by a printing cylinder Thus, images are cyclically formed on the surface of an elongated sheet in its longitudinal direction.

In the manufacture of the sheet material described above, surface defects such as attachment of foreign matters, contamination, pinholes, irregular printing, wrinkles, or the like may occur on the surface of the sheet material.

When a countermeasure is taken against the surface defects, the defects must be detected. In a conventional method, in order to detect the defects, a sheet material of, e.g., a transparent film, on which an image is printed in a color such as milk white is imaged by a camera incorporating a CCD image sensor, and an image signal output from the image sensor is signal-processed. The defects are detected based on the image signal obtained in this manner. In the conventional method, when the detection level of a defect detected by the camera is higher than the detection level of a printed image, the detection level of the camera is determined at an intermediate level between the image detection level and the defect detection level so that the image detection level does not adversely affect the defect detection level.

In the conventional method, when an image has a dark color tone such as black:, red, blue, and the like, the image detection level becomes equal to or higher than the defect detection level Thus, an image is detected as a defect.

In order to eliminate the above drawback, the arrangement sizes and positions of images are measured, and a mask range of a block larger than an image and independent from an outline of each image, e.g., a range extending along a travel direction of a sheet material for each printed character string or extending along the widthwise direction of the sheet material, or an island range, is determined. This range is stored in a memory. During defect detection, the mask range is read out from the memory, and an image detection signal corresponding to this range is masked Thus, a defect on a ground portion of the sheet material on which an image detection signal does not adversely affect image detection can be detected.

With the block masking method, the step of measuring image arrangement sizes and image positions and the step of storing the mask range in the memory are cumbersome. For this reason, when an image is complicated, or when a large number of types of sheet materials are to be subjected to defect detection, the block masking method is not suitable When an image is obliquely printed on the surface of the sheet material, it is found that the mask range cannot be determined. Since a block mask range is determined, portions for which defect detection cannot be performed, by using a background portion of a sheet material between adjacent characters as a starting point, are undesirably increased. When defect detection of such a sheet material is performed, a detection area is decreased, and detection reliability is impaired Since the image is masked and only the background portion of the sheet material is subjected to detection, defect detection of images cannot be performed

SUMMARY OF THE INVENTION

It is an object of The present invention to provide a method and apparatus fOr detecting a significant difference on a surface of a sheet material, which can facilitate defect detection, and has high reliability.

According to the present invention, a sheet material as a to-be-checked material travels, and is imaged by a camera Signal components corresponding to images printed on the sheet material and an outline of a surface defect on the sheet material are extracted from a video signal output from a video camera by an outline extraction circuit. The image and outline signal components are stored in a memory as pattern data for at least one cycle by scrolling write access in accordance with the travel position data of the sheet material. After a preset cycle has passed, the pattern data stored in the memory is read out as outline mask data in accordance with the travel position data The readout outline mask data is compared with present outline pattern data extracted by the outline extraction circuit. Upon making this comparison, the present outline pattern data different from the previous outline pattern data is detected as significant difference data.

In the significant difference detection method, the surface of a traveling sheet material as a to-be-checked material is scanned by a camera in the widthwise direction of the sheet. An outline data component of an image is extracted from an image signal obtained by the camera. When a defect is present on the surface of the sheet material, the outline data component of the defect is extracted from the image signal. With this outline extraction, outline mask data for individually masking the image printed on the sheet material and the defect are detected Pattern data including the outline mask data are sequentially written in the memory in accordance with the travel position data of the sheet material In this manner, pattern data of the sheet material for at least one cycle is written in the memory. The outline pattern data written in the memory serves as a reference pattern for significant difference detection.

The outline patterns are sequentially output from the outline extraction circuit, and the content of the memory is rewritten by scrolling. A comparator compares the latest outline pattern data and immediately preceding outline pattern data stored in the memory, thereby detecting a significant difference between the two outline patterns.

DETAILED DESCRIPTION OF THE PREFERRED EMBODIMENT

Figure 1:
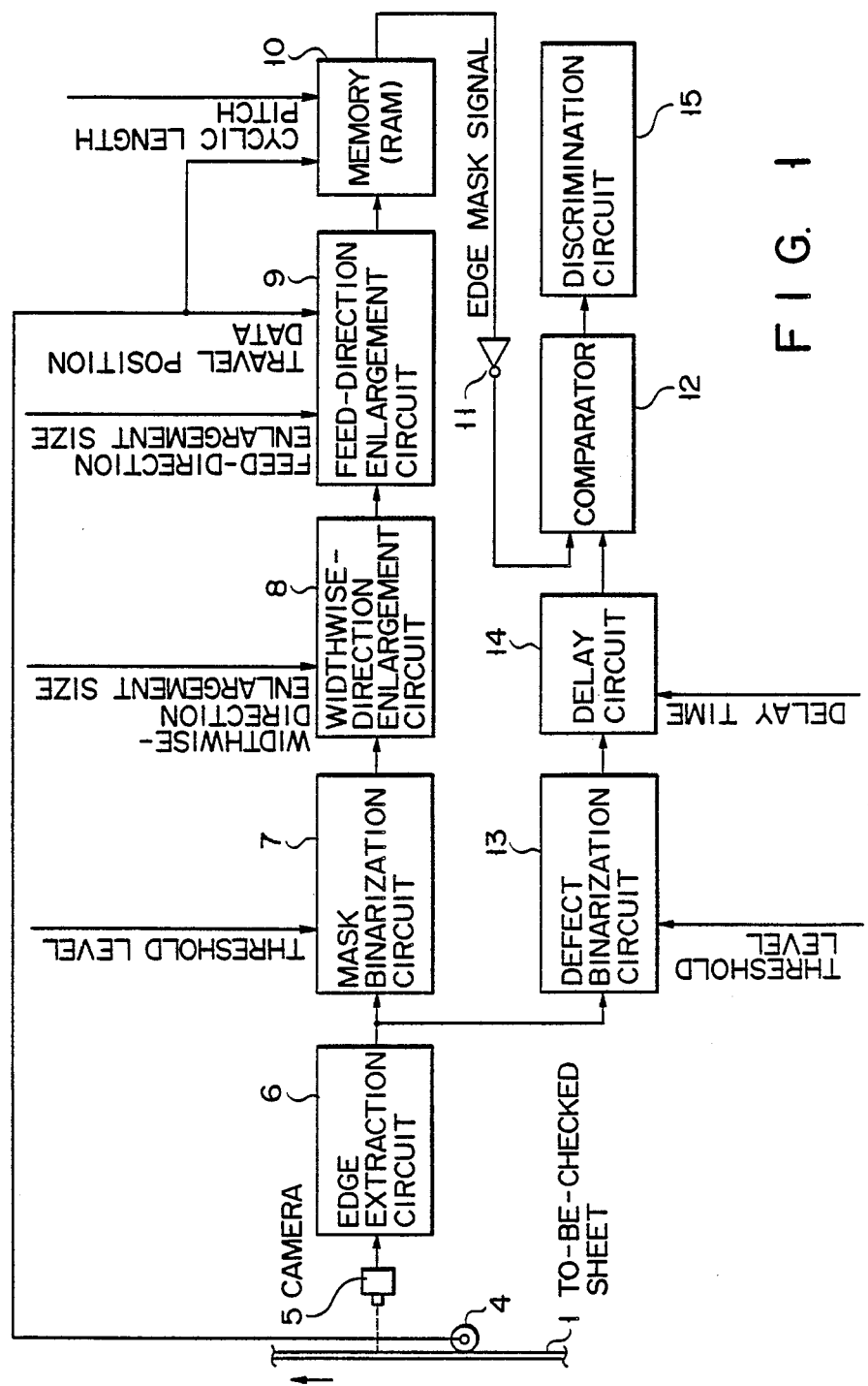
FIG. 1 is a block diagram showing an apparatus for practicing a method of detecting a significant difference on a surface of a to-be-checked sheet according to an embodiment of the present invention.
Figure 2:
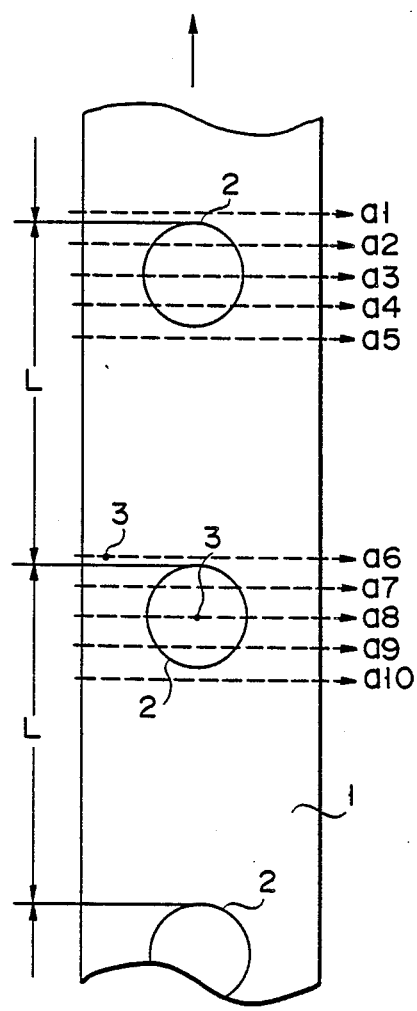
FIG. 2 is a partial plan view of a sheet material.

In FIG. 2, images 2 are printed on a to-be-checked sheet 1 cyclically, i.e., at intervals L. On sheet 1, defect 3 represents attachment of either foreign matter, contamination, pinholes, irregular printing, wrinkles, scratches, or the like. Sheet 1 travels along its longitudinal direction. As shown in FIG. 1, a travel state of sheet 1 is detected by a pulse generator 4 such as a rotary encoder which is in contact with sheet 1.

The surface of sheet 1 is imaged by a camera 5 comprising, e.g., a linear image sensor which receives light transmitted through or reflected by the surface. More specifically, camera 5 scans traveling sheet 1 in the widthwise direction, and outputs a widthwise image signal. Broken arrows a1 to a5 in FIG. 2 indicate scanning positions of a pattern image portion to be scanned first and having one cycle L, and broken arrows a6 to a10 indicate scanning positions of a pattern image portion to be scanned next and having one cycle L.

An image signal output from camera 5 is input to an outline extraction circuit 6 shown schematically in FIG. 1. The output terminal of outline extraction circuit 6 is connected to the input terminal of a mask binarization circuit 7. The output terminal of binarization circuit 7 is connected to a memory (RAM) 10 through a widthwise-direction enlargement circuit 8 and a feed-direction enlargement circuit 9. The output terminal of RAM 10 is connected to one input terminal of a comparator 12 through an inverter 11.

The output terminal of outline extraction circuit 6 is connected to the other input terminal of comparator 12 through a defect binarization circuit 13 and a delay circuit 14. The output terminal of comparator 12 is connected to the input terminal of a discrimination circuit 15.

Outline extraction circuit 6 comprises a differentiation circuit, and is connected to the output terminal of camera 5. Extraction circuit 6 collects all the image signals put out from camera 5, and amplifies the image signals. With this signal emphasizing processing, the outlines of images 2 and defect 3 can be detected.

Binarization circuit 7 binarizes the output from outline extraction circuit 6 in accordance with a threshold level, and outputs a binary signal. The threshold level is set in accordance with the density of an image on sheet 1.

Widthwise-direction enlargement circuit 8 performs the following processing so as not to detect an error when sheet 1 travels in a zig-zag manner within one cyclic length L. In other words, circuit 8 enlarges the output signal from binarization circuit 7 by an amount corresponding to an estimated deviation in the widthwise direction in accordance with the state of a conveying path along which sheet 1 travels. An enlargement size corresponds to several bits each to the right and left in the widthwise direction, and is designated during initialization of the detection apparatus.

Feed-direction enlargement circuit 9 performs the following processing so as not to detect an error when sheet 1 is deviated in a feed (travel) direction within one cyclic length L. In other words, circuit 9 enlarges the output signal from binarization circuit 7 by an estimated deviation in the feed (travel) direction in accordance with the state of the conveying path of sheet 1. In this case, the enlargement size corresponds to the number of pulses put out from pulse generator 4, and is designated during initialization of the detection apparatus. Circuit 9 receives travel position data based on the pulse signal output from pulse generator 4.

Memory 10 comprises, e.g., a RAM which can simultaneously perform read and write access operations by scrolling. The output from outline extraction circuit 6 is written in RAM 10 through circuits 7, 8, and 9. The travel position data obtained based on the output pulses of pulse generator 4 is supplied to memory 10, and the output data from circuit 9 is written in memory 10 in accordance with the travel position data. Cyclic length L of the sheet is input to memory 10 during the initialization of the detection apparatus. Note that memory 10 has a capacity capable of storing pattern data for one cycle of sheet 1.

Data sequentially read out from memory 10 are data representing outline masks. Inverter 11 connected to the output terminal of memory 10 inverts the outline mask data read out from memory 10. The outline pattern data inverted by inverter 11 is input to comparator 12. Comparator 12 comprises an AND gate, and compares the pattern data supplied through inverter 11 with the output data from binarization circuit 13.

Defect binarization circuit 13 converts outline pattern data, exceeding a threshold level, put out from outline extraction circuit 6 into a binary signal. The threshold level is set to be higher than that of the mask binarization circuit 7 in accordance with the image density during initialization of the detection apparatus. Binarization circuit 13 binarizes pattern data for the next cycle which is put out when camera 5 is scanning the sheet 1 and is delayed from cycle L written in memory 10 by, e.g., one cycle.

Delay circuit 14 delays the defect pattern data by a time required for processing mask pattern data through circuits 8 and 9 and memory 10. The pattern data output from delay circuit 14 is input to comparator 12.

Discrimination circuit 15 determines a significant difference as a defect detected by comparator 12, i.e., a width or length of a defect pattern based on the comparison output. In this case, the width of the defect 3 is obtained by measuring a pulse width of the significant difference signal, while the length of the defect 3 is measured by counting scanning lines which scan the defect 3.

In the detection apparatus of the above arrangement, a significant difference as a defect 3 is detected after necessary initialization is performed, i.e., predetermined cyclic length L of an image printed on sheet 1 is set in memory 10 by a keying-in operation, threshold levels are respectively set in binarization circuits 7 and 13 by the keying-in operation, and enlargement sizes in the widthwise and feed directions are respectively set in enlargement circuits 8 and 9 by the keying-in operation.

Figure 4:
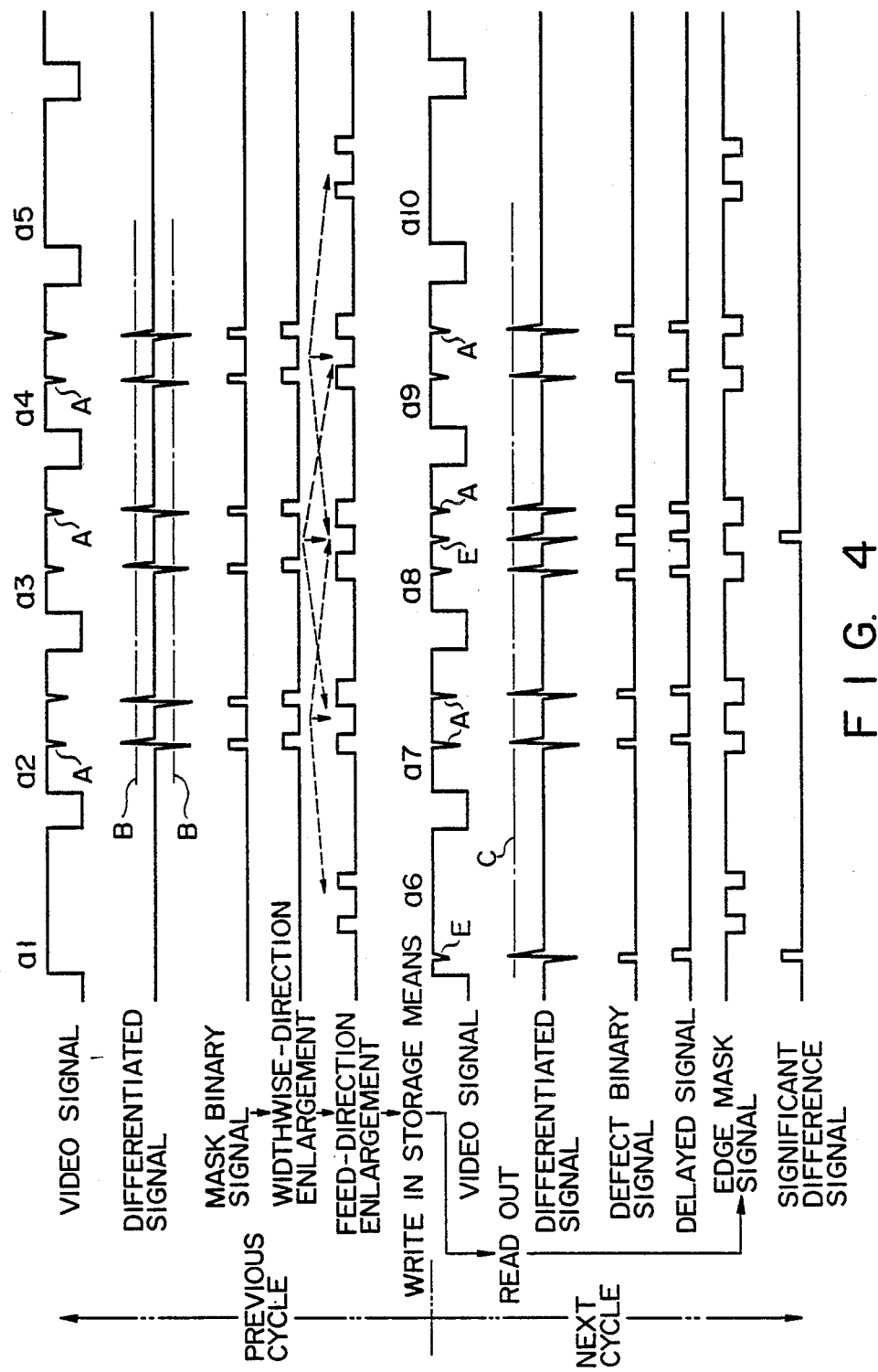
FIG. 4 shows timing charts for explaining an operation of the apparatus shown in FIG. 1.

Upon initiation of detection after initialization, the surface of traveling sheet 1 is scanned in the widthwise direction by camera 5. Camera 5 outputs an image signal corresponding to a widthwise pattern of the sheet. FIG. 4 shows a waveform of an image signal obtained when scanning positions are normal as indicated by arrows a1 to a5 in FIG. 2. In FIG. 4, signal components a1 to a5 of the image signal correspond to the scanning positions in FIG. 2, respectively. Signal component A corresponds to a portion crossing image 2, and indicates a level lower than a background level as a background portion of sheet 1. Such an image signal is output in response to initiation of detection.

The image signal is gathered and differentiated by outline extraction circuit 6. With this processing, a change in signal component A is amplified and an outline of image 2 printed on sheet 1 is extracted. FIG. 4 shows a differentiated signal waveform obtained by outline extraction circuit 6. Signal component B in the differentiated signal indicates a threshold level set in mask binarization circuit 7. At least one of high and low levels B is set.

The differentiated signal for an outline mask extracted for masking image 2 on the surface of sheet 1 along its outline is input to mask binarization circuit 7, and is converted to a mask binary signal, as shown in FIG. 4. The mask binary signal is input to the next widthwise-direction enlargement circuit 8, and is enlarged by several bits in the widthwise direction, as shown in FIG. 4. The binary signal output from circuit 8 is input to feed-direction enlargement circuit 9, and is enlarged in the feed direction by one pulse (one scanning direction) of the pulses put out from pulse generator 4. The enlargement processing is performed as follows. Initially, the mask binary signal is shifted in the feed direction, and the shifted binary signal is added to the nonshifted binary signal. FIG. 4 shows the waveform of the binary signal enlarged in the feed direction. In this waveform, a solid arrow indicates a destination of the mask binary signal, and a broken arrow indicates a shift direction of the mask binary signal.

With this signal enlargement processing, an outline mask for image 2 is enlarged in the widthwise and feed directions. Therefore, changes due to zig-zag travel and elongation, a change in travel speed of sheet 1 can be ignored as a deviation within one cyclic length L of the sheet in the widthwise and feed directions in the enlargement range, thus improving stability of outline masking.

Figure 3:
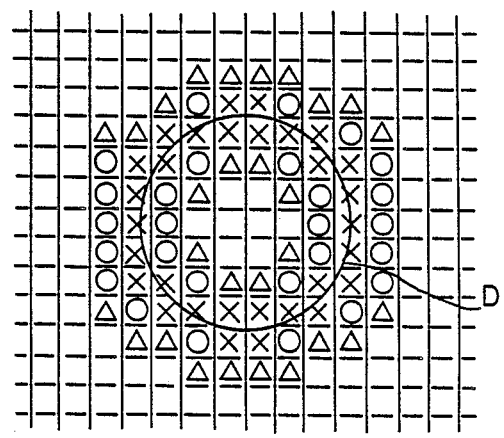
FIG. 3 is a view showing outline mask data stored in a memory arranged in the apparatus shown in FIG. 1.

Pattern data for one cycle including the outline mask data of image 2 obtained as described above is sequentially written in memory 10 in accordance with the travel position data of sheet 1, thus forming an outline mask shown in FIG. 3. In FIG. 3, each digit corresponds to one bit of memory 10. Mark "x" represents a binary signal of differentiated signal D of image 2, mark "o" represents a region enlarged in the widthwise direction, and mark "Δ" represents a region enlarged in the feed direction. More specifically, when a sheet area of a first one cyclic length L is scanned by camera 5, pattern data of image 2 to be masked is stored in memory 10. This storage content serves as a reference pattern for significant difference detection (to be described later).

After the reference pattern is automatically set, the next area of cyclic length L of sheet 1 is scanned by camera 5. Since this cycle includes defect 3, as shown in FIG. 2, a change in signal component E due to defect 3, at which an image signal from camera 5 becomes lower than the background level indicating the background portion of sheet 1, is amplified at scanning positions a6 and a8, as shown in FIG. 4, and both the edges of image 2 printed on sheet 1 and defect 3 are simultaneously extracted. FIG. 4 shows the differentiated signal obtained in this manner In the waveform of this differentiated signal, reference symbol C denotes a threshold level set in defect binarization circuit 13.

The pattern data for one cycle including image 2 to be masked and defect data is enlarged in the widthwise and feed directions and is sequentially written in memory 10 in accordance with the travel position data of sheet 1, thereby updating the content of memory 10. At the same time, memory 10 outputs the pattern data for the previous cycle to comparator 12 through inverter 11 as an outline mask signal. Note that FIG. 4 also shows the outline mask signal inverted by inverter 11.

The output including defect data from outline extraction circuit 6 is input to binarization circuit 13. In this case, the output signal is the latest outline pattern signal obtained upon scanning of camera 5, and is converted to a binary signal by binarization circuit 13, as shown in FIG. 4. The binary signal is delayed by delay circuit 14 to be synchronized with the readout timing of outline mask data from memory 10, and is then inputted to comparator 12 together with the outline mask signal. Comparator 12 compares the outline pattern data for the previous cycle as the reference pattern and the outline pattern data for the next cycle. Only when the background signal of the reference pattern coincides with the defect signal, comparator 12 outputs a comparison result signal, as shown in FIG. 4. The comparison result signal from comparator 12 indicates a significant difference from the pattern data for the previous cycle. The significant difference data representing a defect 3 detected in this manner is inputted to discrimination circuit 15, and the length or width of the defect 3 is determined. Thereafter, a discrimination result is put out from an output apparatus such as a printer.

With the significant difference detection method described above, since outline pattern data of image 2 of sheet 1 is automatically retrieved and stored in memory 10, positions of a plurality of images printed on a sheet 1 need not be individually designated, and their position data need not be prestored in a memory 10. In other words, cyclic length L need only be set in memory 10, and then a significant difference can be automatically detected. Therefore, when a significant difference is detected for a large number of types of to-be-checked sheets 1 or a to-be-checked sheet 1 on which complicated images are printed, cyclic length L need only be set in memory 10, and the significant difference can be automatically detected, resulting in easy operation of the detection apparatus.

Since the storage content of memory 10 is sequentially and automatically updated, even if a to-be-checked sheet 1 travels in a zig-zag manner, the detection apparatus does not suffer from the influence of the zig-zag travel.

Since the mask area of image 2 is used as a mask, an area to be masked can be reduced, and an area to be detected can be increased, thus improving detection reliability.

In this embodiment, since image 2 is formed by thin lines, and edges at two ends of each line are regarded to coincide with each other, only a defect 3 on a background portion of sheet 1 is detected as a significant difference. If image 2 is formed by a bold line or wide pattern, and edges at two ends of each bold line or wide pattern are separated from each other, a defect 3 in the images 2 overlapping between these edges can be processed in the same manner as a defect 3 in a background portion. Thus, such a defect 3 can be detected. Even when a defect 3, e.g., either an omission, extension, or connection is formed due to an error during an image formation on sheet 1, a significant difference is detected upon comparison between the reference pattern data for the previous cycle and the pattern data for the next cycle Thus, a defect 3 of an image 2 itself can be detected as a significant difference.

According to the significant difference detection method of the present invention, a significant difference between the reference pattern which is read out as soon as it is written in the memory and the latest outline pattern obtained by camera 5 is detected for each raster. For the purpose of definition, a raster is the area on which the image 2 is reproduced. Thus, a significant difference can be detected in real time. As a result, detection speed is high and significant difference detection for the entire surface of the sheet material can be realized at high speed.

In this invention, when an image signal from camera 5 is A/D converted, outline extraction circuit 6 may comprise a digital circuit for executing a Laplacian outline detection scheme In this case, binarization circuits 7 and 13 are replaced with the outline extraction circuit.

In the above embodiment, the step of enlarging the outline mask zone may be omitted. Furthermore, pattern data for a cycle immediately preceding a cycle to be detected is used as reference pattern data. However, a reference cycle may be a more previous cycle.

The present invention can be applied to significant difference detection for a to-be-checked sheet on which embossed images having a three-dimensional pattern are cyclically formed.

According to the present invention, an outline of an image 2 printed on a sheet material 1 is extracted by an outline extraction circuit, and an outline masking area corresponding to the extracted outline pattern is determined. The outline pattern data obtained in this outline extraction step is stored in a memory 10, and the pattern data stored in this memory 10 is updated for each cycle. Pattern data for the previous cycle which is read out from the memory 10 in response to updating is compared, as a reference pattern, with the latest input outline pattern data. Thus, a significant difference is detected from these outline pattern data. Therefore, the step of measuring image arrangement sizes and image positions for determining a mask range and the step of storing the mask range in a memory, which steps are necessary in the conventional method, can be omitted. A necessary and minimum masking area can be set by outline masking, and a detection area can be increased. Furthermore, since a significant difference of an image 2 itself can be detected, reliability in significant difference detection can be improved.

What is claimed is:

1. A method of detecting a significant difference of a to-be-checked sheet, comprising the steps of:
    conveying the to-be-checked sheet on which images are cyclically printed in a longitudinal direction of travel;
    scanning sequentially the image on the traveling to-be-checked sheet by a single imaging means to obtain sequentially image data corresponding to the image;
    extracting outline data, representing an outline of each of the images and an outline of at least one defect on the to-be-checked sheet, from the image data;
    outputting travel position data indicating a travel position of the to-be-checked sheet;
    writing the outline data, extracted in the step of extracting the outline data, in a storage means with a predetermined cycle in accordance with the travel position data;
    reading out the outline data;
    comparing the outline data for a preceding cycle, read out from the storage means as outline mask data, with latest outline data outputted from an outline extraction means and obtained in the predetermined cycle following the preceding cycle; and
    detecting a significant difference between the outline mask data and the latest outline data in accordance with a comparison result obtained in the comparing step.

2. A method according to claim 1, wherein the step of scanning sequentially the images to obtain the image data including the substep of scanning the to-be-checked sheet in a widthwise direction.

3. A method of detecting a significant difference of a to-be-checked sheet, comprising the steps of:
    causing the to-be-checked sheet on which images are cyclically printed in a longitudinal direction to travel;
    scanning the traveling to-be-checked sheet by imaging means to obtain image data including the image;
    extracting outline data representing an outline of the image and an outline of a defect on the to-be-checked sheet from the image data;
    outputting travel position data indicating a travel position of the to-be-checked sheet;
    writing the outline data extracted in the step of extracting the outline data in storage means with a predetermined cycle in accordance with the travel position data and simultaneously reading out the outline data;
    comparing the outline data for an immediately preceding cycle read out from said storage means as outline mask data with latest outline data output from said outline extraction means and obtained in c cycle following the immediately preceding cycle; and
    detecting a significant difference between the outline mask data and the latest outline data in accordance with the comparison result obtained in the comparison step;
    wherein the step of writing the outline data comprises the step of enlarging the outline data extracted in the step of extracting the outline data in a widthwise direction of the to-be-checked sheet so as to compensate for an estimated deviation in the widthwise direction, and the step of enlarging the outline data in a feed direction of the to-be-checked sheet in order to compensate for an estimated deviation in a travel direction.

4. A method according to claim 1, wherein the comparing step includes the substep of delaying latest outline data by a predetermined period of time so as to be synchronized with a readout timing of the outline mask data.

5. An apparatus for detecting a significant difference of a to-be-checked sheet, comprising:

means for conveying the to-be-checked sheet on which multiple images are cyclically printed in a longitudinal direction of travel;

means for scanning sequentially the images on the traveling to-be-checked sheet to output a plurality of image data signals corresponding to the multiple images;

means for extracting an outline of each of the multiple images and an outline of at least one defect on the to-be-checked sheet from the image data signals;

means for outputting travel position data indicating a travel position of the to-be-checked sheet;

storage means, in which the outline data extracted by the outline extracting means is sequentially written with a predetermined cycle in accordance with the travel position data, and from which outline data is simultaneously read out;

means for comparing the outline data for a preceding cycle, read out from the storage means as outline mask data, with latest outline data outputted from the outline extracting means and obtained in the predetermined cycle following the preceding cycle; and means for detecting a significant difference between the outline mask data and the latest outline data in accordance with a comparison result obtained by the comparing means.

6. An apparatus according to claim 5, wherein the scanning means for outputting the plurality of image data signals includes means for imaging the to-be-checked sheet in a widthwise direction.

7. An apparatus, comprising:

means for causing the to-be-checked sheet on which images are cyclically printed in a longitudinal direction to travel;

means for scanning the traveling to-be-checked sheet to output an image data signal corresponding to the image;

means for extracting an outline of the image and an outline of a defect on the to-be-checked sheet from the image data signal;

means for outputting travel position data indicating a travel position of the to-be-checked sheet;

storage means in which the outline data extracted by said outline extraction means is sequentially written with a predetermined cycle in accordance with the travel position data and from which the outline data is simultaneously read out;

means for comparing the outline data for an immediately preceding cycle read out from said storage means as outline mask data with latest outline data output from said outline extraction means and obtained in a cycle following the immediately preceding cycle; and means for detecting a significant difference between the outline mask data and the latest outline data in accordance with the comparison result obtained by said comparison means;

wherein means for enlarging the outline data extracted by said outline extraction means in a widthwise direction of the to-be-checked sheet so as to compensate for an estimated deviation in the widthwise direction, and means for enlarging the outline data in a feed direction of the to-be-checked sheet in order to compensate for an estimated deviation in a travel direction are enlarged between said outline extraction means and said storage means.

8. An apparatus according to claim 5, wherein a means for delaying the latest outline data by a predetermined period of time to be synchronized with a readout timing of the outline mask data is arranged between the comparing means and the outline extracting means.

9. A method of detecting a significant difference of a to-be-checked sheet, comprising the steps of:

conveying the to-be-checked sheet on which images are cyclically printed in a longitudinal direction of travel;

scanning the images on the traveling to-be-checked sheet by an imaging means for obtaining image data corresponding to the images;

extracting outline data, representing an outline of each of the images and an outline of at least one defect on the to-be-checked sheet, from the image data;

outputting travel position data indicating a travel position of the to-be-checked sheet;

enlarging the outline data, in a widthwise direction of the to-be-checked sheet, to compensate for an estimated deviation in the widthwise direction, enlarging the outline data, in the longitudinal direction of travel of the to-be-checked sheet, to compensate for an estimated deviation in the longitudinal direction;

writing enlarged outline data in a storage means with a predetermined cycle in accordance with the travel position data;

reading out the outline data;

comparing the enlarged outline data for a preceding cycle read out from the storage means as an outline mask data, with latest outline data outputting during the outline data extracting step and obtained in the predetermined cycle following the preceding cycle; and detecting a significant difference between the outline mask data and the latest outline data in accordance with a comparison result obtained in the comparing step.

10. A method according to claim 9, wherein the step of scanning the images includes a substep of scanning the to-be-checked sheet in a widthwise direction.

11. A method according to claim 9, wherein the comparing step includes a substep of delaying the latest outline data by a predetermined period of time so that an output of the latest outline data is synchronized with a readout timing of the outline mask data.

12. An apparatus for detecting a significant difference of a to-be-checked sheet, comprising:

means for conveying the to-be-checked sheet on which images are cyclically printed in a longitudinal direction of travel;

means for scanning the images on the traveling to-be-checked sheet by imaging means for outputting image data corresponding to the images;

means for extracting outline data, representing an outline of each of the images and an outline of at least one defect on the to-be-checked sheet, from the image data;

means for outputting travel position data indicating travel positions of the to-be-checked sheet;

means for enlarging the outline data in a widthwise direction of the to-be-checked sheet, to compensate for an estimated deviation in the widthwise direction;

means for enlarging the outline data in the longitudinal direction of travel of the to-be-checked sheet, to compensate for an estimated deviation in the longitudinal direction;

means for writing enlarged outline data in a storage means with a predetermined cycle in accordance with the travel position data;

reading out the outline data;

means for comparing enlarged outline data for a preceding cycle, read out from the storage means as outline mask data, with the latest outline data outputting from the outline data extracting means and obtained in the predetermined cycle following the preceding cycle; and means for detecting a significant difference between the outline mask data and the latest outline data in accordance with a comparison result obtained by the comparing means.

13. An apparatus according to claim 12, wherein the scanning means includes means for scanning the to-be-checked sheet in a widthwise direction.

14. An apparatus according to claim 12, wherein the comparing means includes means for delaying the latest outline data by a predetermined period of time so that an output of the latest outline data is synchronized with a readout timing of the outline mask data.

* * * * *